(12) United States Patent
Ismail et al.

(10) Patent No.: US 6,501,006 B1
(45) Date of Patent: Dec. 31, 2002

(54) NUCLEIC ACIDS CONFERRING CHILLING TOLERANCE

(75) Inventors: Abdelbagi M. Ismail, Riverside, CA (US); Anthony E. Hall, Riverside, CA (US); Timothy J. Close, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/436,434

(22) Filed: Nov. 8, 1999

(51) Int. Cl.[7] .................. C12N 05/09; C12N 15/29; C12N 15/82; A01H 5/00
(52) U.S. Cl. .................. 800/289; 800/278; 800/298; 800/295; 536/23.1; 536/24.1; 536/23.6; 435/69.1; 435/320.1; 435/419; 435/468
(58) Field of Search .................. 800/278, 289, 800/298, 295; 536/23.1, 24.1, 23.6; 435/69.1, 320.1, 419, 468

(56) References Cited

U.S. PATENT DOCUMENTS 5,837,545 A * 11/1998 Guy et al. .................. 435/419

OTHER PUBLICATIONS

Iuchi et al, "Novel Drought–Inducible Genese in the Highly Drought–tolerant Cowpea: Cloning of cDNAs and Analysis of the Expression of the Corresponding Genes", 1996 Plant Cell Physiol vol. 37 No. 8 pp. 1073–1082.*
Kaye et al, "Characterization of a Gene for Spinach CAP160 and Espression of Two Spinach Cold–Acclimation Proteins in Tobacco", 1998 vol. 116 pp. 1367–1377.*
Blackman, et al., "Desiccation tolerance in deveploping soybean seeds: The role of stress proteins," Physiol. Plant., 93:630–638 (1995).
Bramlage, et al., "Chilling Stress to Soybeans during Imbibition," Plant Physiol., 61:525–529 (1978).
Chen, et al., "Role of Carbohydrates in Desiccation Tolerance and Membrane Behavior in Maturing Maize Seed," Crop Sci., 30:971–975 (1990).
Close, "Dehydrins: A commonalty in the response of plants to dehydration and low temperature," Physiol. Plant., 100:291–296 (1997).
Close, "Dehydrins:Emergence of a biochemical role of a family of plant dehydration proteins," Physiol. Plant., 97:795–803 (1996).
Danyluk, et al., "Accumulation of an Acidic Dehydrin in the Vincinity of the Plasma Membrane during Cold Acclimation of Wheat," The Plant Cell, vol. 10:623–638 (Apr. 1998).
Egerton–Warburton, et al., "Temporal accumulation and ultrastructural localization of dehydrins in Zea mays," Physiol. Plant., 101:545–555 (1997).
Ingram, et al., "The Molecular Basis of Dehydration Tolerance in Plants," Annu. Rev. Plant Physiol. Plant Mol. Biol., 47:377–403 (1996).
Ismail, et al., "Positive and Potential Negative Effects of Heat–Tolerance Genes in Cowpea," Crop Sci., 38:381–390 (1998).
Ismail, et al., "Chilling Tolerance during Emergence of Cowpea Associated with a Dehydrin and Slow Electrolyte Leakage," Crop Sci., 37:1270–1277 (1997).
Koster, et al., "Sugars and Desiccation Tolerance in Seeds, "Plant Physiol., 88:829–832 (1988).
Leopold, "Temperature Effects on Soybean Imbibition and Leakage," Plant Physiol., 65:1096–1098 (1980).

* cited by examiner

Primary Examiner—Phuong T. Bui
Assistant Examiner—Medina A.. Ibrahim
(74) Attorney, Agent, or Firm—Townsend & Townsend & Crew LLP (57) ABSTRACT

The present invention provides isolated nucleic acid molecules comprising a polynucleotide sequence encoding a DHN polypeptide that enhances chilling tolerance in plants.

8 Claims, 3 Drawing Sheets

| | | | | | |
|---|---|---|---|---|---|
| MASYQKQYED | QGCKIDEYGN | VVQETDEYGN | PVHAASVTYI | TSTTGGLGDD | 50 |
| TNKQHDTSNV | YGADTRRQHG | TIGDTGRQHG | TTGGFTGDTG | RQYGTTGGFT | 100 |
| GDTGRQHGTT | GGFTGDTGKQ | HGTTGGFTGD | TGRQHGTTGG | FTGDTGRQHG | 150 |
| TTGDTGRQHG | TTGGFTGGDT | GLGGPYVGAN | TADTGTGPRS | GTTGGSAYGS | 200 |
| GGYGSGAGAG | YGMNTGGAHS | DERYGREYRE | HDQSRGDHDK | KGIVDKIKEK | 250 |
| LPGGHSDNK | | | | | 259 |

NUCLEIC ACIDS CONFERRING CHILLING TOLERANCE

STATEMENT AS TO RIGHTS TO INVENTIONS MADE UNDER FEDERALLY SPONSORED RESEARCH AND DEVELOPMENT

This invention was made with Government support under Grant Nos. 9205269 awarded by the National Science Foundation and 94-37100-0688 awarded by the United States Department of Agriculture. The Government has certain rights in this invention.

FIELD OF THE INVENTION

This invention relates to plant genetic engineering and plant breeding. In particular, it relates to methods of modulating chilling tolerance in plants

BACKGROUND OF THE INVENTION

The prior art lacks means for enhancing seed emergence in cool soils by expressing of genes associated with endomembrane integrity. The present invention addresses these and other needs.

Tropical crops such as cotton, maize, and cowpea, are sensitive to chilling soil temperatures often encountered during early sowing in subtropical regions in spring. Early spring sowing can be beneficial in the subtropics because it results in a longer growing season and higher yields. However, early sown seeds that are subjected to chilling temperatures suffer reductions in rate of emergence and maximal emergence. Variation in chilling sensitivity at germination has been found among genotypes of warm season annuals such as cowpea (Ismail et al., *Crop Sci.* 37:1270–1277 (1997)), soybean (Ismail et al. *Crop Sci.* 37:1270–1277 (1997)), cotton (Christiansen, M. N. & Lewis, C. F., *Crop Sci.* 13:210–212 (1973)) and maize (Cal, J. P. & Obendorf, R. L., *Crop Sci.* 12:369–373 (1972)). Numerous studies have suggested positive associations between the extent of electrolyte leakage from seeds and pre-emergence mortality of embryos at chilling temperature for chilling sensitive crops (Bramlage et al., *Plant Physiol.* 61:525–529 (1978); Leopold, A. C., *Plant Physiol.* 65:1096–1098 (1980)).

Soluble sugars (Koster, K. L., & Leopold, A. C., *Plant Physiol.* 88:829–832 (1988); Chen, Y., & Burris, J. S., *Crop Sci.* 30:971–975 (1990)) and proteins, typically LEA (late embryogenesis-abundant) (Blackman et al., *Physiol. Plant.* 93:630–638 (1995); Close, T. J., *Physiol. Plant.* 97:795–803 (1996); Close, T. J., *Physiol. Plant.* 100:291–296 (1997); Ingram, J. & Bartels, D., *Annu. Rev. Plant Physiol. Plant Mol. Biol.* 47:377–403 (1996)) are known to accumulate during seed development and are thought to play a role in protecting the embryo during desiccation. Studies with soybean indicated that accumulation of LEA proteins during embryogenesis might reduce the extent of desiccation-induced electrolyte leakage in immature seeds suggesting a role in membrane protection (Blackman et al., *Physiol. Plant.* 93:630–638 (1995)). Dehydrins (DHN, LEA D11 family) are among the most commonly observed proteins induced by environmental stress associated with dehydration or low temperature (Close, T. J., *Physiol. Plant.* 97:795–803 (1996); Close, T. J., *Physiol. Plant.* 100:291–296 (1997)). Distinct subclasses of DHNs have been noted (Close, T. J., *Physiol. Plant.* 100:291–296 (1997)). Several lines of evidence suggested a role of DHNs in membrane interactions and/or protein stabilization (Ismail et al., *Crop Sci.* 37:1270–1277 (1997); Close, T. J., *Physiol. Plant.* 100:291–296 (1997); Egerton-Warburton et al., *Physiol. Plant.* 101:545–555 (1997); Danyluk et al., *Plant Cell.* 10:623–638 (1998)).

In cowpea, two closely related lines ($F_6$ siblings) were found to vary in maximal emergence under chilling field conditions (Ismail et al., *Crop Sci.* 37:1270–1277 (1997)), but also in other characters (Ismail, A. M. & Hall, A. E., *Crop Sci.* 38:381–390 (1998)). Dry, mature seeds of the chilling-tolerant line, 1393-2-11, were found to contain a substantial quantity (estimated to be about 1% of total soluble protein) of a ~35-kDa DHN protein that was not detectable in the seeds of the genetically similar line, 1393-2-1. Also the chilling-tolerant line had slower electrolyte leakage from its seeds during imbibition at low temperature. Based on studies with reciprocal hybrids, the chilling tolerance of 1393-2-11 was hypothesized to be due to additive and independent effects of the DHN under dominant nuclear inheritance and a maternal effect associated with slower electrolyte leakage from seeds during imbibition compared with line 1393-2-1 (Ismail et al., *Crop Sci.* 37:1270–1277 (1997)).

Despite these advances, the prior does not provide nucleic acids useful for conferring chilling tolerance on seedlings during and after emergence in soil. The present invention addresses these and other needs.

SUMMARY OF THE INVENTION

The present invention provides isolated nucleic acid molecules comprising a polynucleotide sequence encoding a DHN polypeptide that enhances chilling tolerance in plants. The proteins comprise an amino acid sequence as shown in SEQ ID NO:2. The nucleic acid encoding the protein preferably has a polynucleotide sequence that specifically hybridizes to SEQ ID NO: 1. The invention also provides recombinant expression cassettes comprising the polynucleotide sequences of the invention. The expression cassettes typically comprise a seed-specific promoter or promoter from the allele described here.

The invention also provides transgenic plants comprising a recombinant expression cassette comprising a promoter operably linked to the polynucleotide sequence. The transgenic plants of the invention can be, for example, cowpea. In addition, marker assisted selection as described here can be used to identify related genes and alleles in other plants. Using these markers one of skill can use conventional breeding techniques to confer chilling tolerance to a variety of plant species. Such methods are particularly useful in other members of the legume family, such as soybean.

DEFINITIONS

The term "DHN polypeptide" refers to polypeptides having at least substantial identity to SEQ ID NO: 2 and that confer chilling tolerance on plant seedlings. As discussed in more detail below, DHN polypeptides of the invention, and the genes that encode them, are distinct from other allelic variants in a number of ways. Among the differences is the presence of one additional Φ-segment ($Φ_7$). The general structure of these proteins, and in particular Φ-segments, is discussed in detail in Close, T. J., *Physiol. Plant.* 100:291–296 (1997).

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

The term "promoter" refers to regions or sequence located upstream and/or downstream from the start of transcription and which are involved in recognition and binding of RNA polymerase and other proteins to initiate transcription. A "plant promoter" is a promoter capable of initiating transcription in plant cells. Such a promoter can be derived from plant genes or from other organisms, such as viruses capable of infecting plant cells.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety).

A polynucleotide "exogenous to" an individual plant is a polynucleotide which is introduced into the plant by any means other than by a sexual cross. Examples of means by which this can be accomplished are described below, and include Agrobacterium-mediated transformation, particle-mediated methods, electroporation, and the like. Such a plant containing the exogenous nucleic acid is referred to here as a $T_1$ (e.g. in Arabidopsis by vacuum infiltration) or $R_0$ (for plants regenerated from transformed cells in vitro) generation transgenic plant. Transgenic plants that arise from sexual cross or by selfing are descendants of such a plant.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998)) of an isolated nucleic acid comprising the expression cassette. In another example, a recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11–17 (1988) e.g., as implemented in the program PC/GENE (Intelligenetics, Mountain View, Calif., USA).

The phrase "substantially identical," in the context of two nucleic acids or polypeptides, refers to sequences or subsequences that have at least 60%, preferably 70%, more preferably 80%, most preferably 90–95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides display significant variation. Therefore a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. AppL Math*. 2:482 (1981), by the homology alignment algorithm of Needleman & Wunsch, *J Mol. Biol*. 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *j. Mol. Biol*. 215: 403–410 and Altschuel et al. (1977) *Nucleic Acids Res*. 25: 3389–3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word bits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached The BLAST algorithm parameters W, T, and X determine the sensitivity and speed of the alignment. The BLASTN program (for nucleotide sequences) uses as cefaults a wordlength (W) of 11, an expectation (E) of 10, M5, N=4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, Proteins (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10 C. lower than the thermal melting point ($T_m$) for the specific sequence at a defined ionic strength pH. Lower stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions.

In the present invention, genomic DNA or cDNA comprising nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., an RNA gel or DNA gel blot hybridization analysis.

BRIEF DESCRIPTION OF THE DRAWINGS

FIG. 2 (*a*) shows the deduced amino acid sequence of the ~35-kDa cowpea dehydrin cDNA with the amino acid sequence of the putative coding region presented in a single-letter code (SEQ ID NO: 2). The Φ-segment landmarks are shown in boldface. FIG. 2 (*b*) shows a schematic representation showing the $Y_2K$ structure with eight repeats (Φ-segments), six of them with 14 amino acid residues and two with 10 residues each. Arrows indicate positions of the PCR primers. (c) PCR products from each line; note that $\Phi_7$ is deleted in the alleles represented by smaller PCR products.

DETAILED DESCRIPTION

As noted above, a genetic association between the presence of a ~35-kDa protein in mature seed and chilling tolerance during seedling emergence has been observed (Ismail et al., *Crop Sci.* 37:1270–1277 (1997)). Accumulation of this protein in developing seeds is coordinated with the start of the dehydration phase of embryo development, and the characteristics of the purified protein indicated that it is a DHN (Ismail et al., *J. Plant Physiol.* 120, 237–244 (1999)). Among other properties, this DHN has been found (Ismail et al., T. J. *Plant Physiol.* 120, 237–244 (1999)) to adhere to other polypeptides under specific salt conditions and also to adopt an α-helical structure in the presence of SDS.

The present invention is based, at least in part, on genetic evidence of the association between one allele of the structural gene, Dhn1, encoding this DHN protein and the chilling tolerance trait. This allele is referred to as the DHN present allele. In addition, the invention provides nucleic acids encoding this protein. Thus the invention also provides methods for producing transgenic plants with enhanced chilling tolerance. The approach described here can also be used to identify relevant markers to use in marker-assisted selection of desired genotypes in any plant. This approach is particularly valuable in identifying the genotype in warm season crops such as maize, rice, sorghum, soybean and cotton.

Increasing Polypeptide Activity or Gene Expression

Any of a number of means well known in the art can be used to increase the concentration of the 35 kd DHN protein in plant cells. Usually isolated nucleic acid sequences prepared as described herein are used to prepare recombinant expression cassettes in recombinant vectors. The vectors are introduced into plant cells using methods well known to those of skill in the art. Preparation of suitable constructs and means for introducing them into plants are described below.

One of skill will recognize that the polypeptides encoded by the nucleic acids of the invention, like other proteins, have different domains that perform different functions. Thus, gene sequences of the invention need not be full length, so long as the desired functional domain of the protein is expressed.

Modified protein chains can also be readily designed utilizing various recombinant DNA techniques well known to those skilled in the art and described in detail below. For example, the chains can vary from the naturally occurring sequence at the primary structure level by amino acid substitutions, additions, deletions, and the like. These modifications can be used in a number of combinations to produce the final modified protein chain.

In addition to genetic engineering techniques, endogenous genes can be modified to enhance expression of the desired polypeptide. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays, fast neutrons or gamma rays can be used.

Alternatively, homologous recombination can be used to induce targeted gene modifications by specifically targeting gene of the invention in vivo (see, generally, Grewal and Klar, *Genetics* 146: 1221–1238 (1997) and Xu et al., *Genes Dev.* 10: 2411–2422 (1996)). Homologous recombination has been demonstrated in plants (Puchta et al., *Experientia* 50: 277–284 (1994), Swoboda et al., *EMBO J.* 13: 484–489 (1994); Offringa et al., *Proc. Natl. Acad. Sci. USA* 90: 7346–7350 (1993); and Kempin et al. *Nature* 389:802–803 (1997)).

Other means for increasing activity of polynucleotides and polypeptides of the invention can also be used. For example, one method to increase expression of genes of the invention is to use "activation mutagenesis" (see, e.g. Hiyashi et al. *Science* 258:1350–1353 (1992)). In this method an endogenous gene of the invention can be modified to be expressed constitutively, ectopically, or excessively by insertion of T-DNA sequences that contain strong/constitutive promoters upstream of the endogenous gene.

Inhibition of Activity or Expression of Polynucleotides or Polypeptides of the Invention Activity of endogenous genes an also be inhibited using well known techniques. Inhibition of expression of these genes can be used to inhibit seed germination and thus control the timing of seed germination, for example, by using an inducible promoter to control expression of the nucleic acids in recombinant expression cassettes of the invention.

The nucleic acid sequences disclosed here can be used to design nucleic acids useful in a number of methods to inhibit expression of genes of the invention in plants. For instance, antisense technology can be conveniently used. To accomplish this, a nucleic acid segment from the desired gene is cloned and operably linked to a promoter such that the antisense strand of RNA will be transcribed. The construct is then transformed into plants and the antisense strand of RNA is produced. In plant cells, it has been suggested that antisense suppression can act at all levels of gene regulation including suppression of RNA translation (see, Bourque, *Plant Sci.* (Limerick) 105: 125–149 (1995); Pantopoulos, In Progress in Nucleic Acid Research and Molecular Biology, Vol. 48. Cohn, W. E. and K. Moldave (Ed.). Academic Press, Inc.: San Diego, Calif., USA; London, England, UK. p. 181–238; Heiser et al., *Plant Sci.* (Shannon) 127: 61–69 (1997)) and by preventing the accumulation of mRNA which encodes the protein of interest, (see, Baulcombe, *Plant Mol. Bio.* 32:79–88 (1996); Prins and Goldbach, *Arch. Virol.* 141: 2259–2276 (1996); Metzlaff et al. *Cell* 88: 845–854 (1997), Sheehy et al., *Proc. Nat. Acad. Sci. USA*, 85:8805–8809 (1988), and Hiatt et al., U.S. Pat. No. 4,801, 340).

Another well-known method of suppression is sense co-suppression. Introduction of nucleic acid configured in the sense orientation has been recently shown to be an effective means by which to block the transcription of target genes. For an example of the use of this method to modulate expression of endogenous genes (see, Assaad et al., *Plant Mol. Bio.* 22: 1067–1085 (1993); Flavell, *Proc. Natl. Acad. Sci. USA* 91: 3490–3496 (1994); Stam et al., *Annals Bot.* 79: 3–12 (1997); Napoli et al., *The Plant Cell* 2:279–289 (1990); and U.S. Pat. Nos. 5,034,323, 5,231,020, and 5,283,184).

Other means of inhibiting expression are known. These methods include formation of triple-helix DNA (see, e.g., Havre and Glazer *J. Virology* 67:7324–7331 (1993); Scanlon et al. *FASEB J.* 9:1288–1296 (1995); Giovannangeli et al. *Biochemistry* 35:10539–10548 (1996); Chan and Glazer *J. Mol. Medicine* (Berlin) 75: 267–282 (1997)) and ribozymes (Zhao and Pick, *Nature* 365:448–451 (1993); Eastham and Ahlering, *J. Urology* 156:1186–1188 (1996); Sokol and Murray, *Transgenic Res.* 5:363–371 (1996); Sun et al., *Mol. Biotechnology* 7:241–251 (1997); and Haseloff et al., *Nature*, 334:585–591 (1988)).

Modification of endogenous genes can also be used to inhibit expression.

Methods for introducing genetic mutations described above can also be used to select for plants with decreased expression of genes of the invention.

Other means for inhibiting polynucleotide or polypeptide activity can also be used. Activity of polynucleotides of the invention may be modulated by eliminating the proteins that are required for cell-specific expression of such polynucleotides. Thus, expression of regulatory proteins and/or the sequences that control gene expression can be modulated using the methods described here.

Purification of Polypeptides

Naturally occurring or recombinant 35 kD DHN polypeptides of the invention can be purified for a variety of purposes, e.g. for use in functional assays. Naturally occurring polypeptides can be purified, e.g., from plant tissue and any other source of the desired polypeptide as described for instance in Ismail et al., *Plant Physiol.* 120, 237–244 (1999). Recombinant polypeptides can be purified from any suitable expression system.

The polypeptides of the invention may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant polypeptides are being purified. For example, proteins having established molecular adhesion properties (e.g. epitope tags, histidine tags and the like) can be reversibly fused to polypeptides of the invention. With the appropriate ligand, the such polypeptides can be selectively adsorbed to a purification column and then freed from the column in a relatively pure form.

Isolation of Nucleic Acids of the Invention

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998).

The isolation of nucleic acids of the invention may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as seeds, and a cDNA library that contains a gene transcript of the invention is prepared from the mRNA. Alternatively, cDNA may be prepared from mRNA extracted from other tissues in which genes of the invention or homologs are expressed. The cDNA or genomic library can then be screened using a probe based upon the sequence of a cloned gene of the invention as disclosed here. Probes may be used to hybridize with genomic DNA or cDNA sequences to isolate homologous genes in the same or different plant species. Alternatively, antibodies raised against a polypeptide of the invention can be used to screen an MRNA expression library.

Genomic clones identified in this way can then be used to isolated promoter sequences from the genes of the invention. Once a desired genomic clone is identified, the 5' sequences can be analyzed to identify the promoter sequence from the gene. This can be accomplished using deletion analysis and a promoterless reporter gene (e.g., GUS) to identify those regions which can drive expression of a structural gene. Sequences characteristic of promoter sequences can also be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site.

Alternatively, the nucleic acids of interest can be amplified from nucleic acid samples using amplification techniques. For instance, polymerase chain reaction (PCR) technology can be used to amplify the sequences of genes of the invention directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired MRNA in samples, for nucleic acid sequencing, or for other purposes. For a general overview of PCR, see *PCR Protocols: A Guide to Methods and Applications*. (Innis, M, Gelfand, D., Sninsky, J. and White, T., eds.), Academic Press, San Diego (1990). Appropriate primers and probes for identifying sequences of the invention from plant tissues are generated from comparisons of the sequences provided here.

Polynucleotides may also be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumefaciens*, and other transcription initiation regions from various plant genes known to those of skill.

Alternatively, the plant promoter may direct expression of a nucleic acid of the invention in a specific tissue, organ or cell type (i.e. tissue-specific promoters) or may be otherwise under more precise environmental or developmental control (i.e. inducible promoters). Examples of environmental conditions that may effect transcription by inducible promoters include anaerobic conditions, elevated temperature, the presence of light, or application of chemicals/hormones (such promoters can be used, for example, in the chemical induction of antisense sequences for inhibition of seed germination until a desired time). Exemplary promoters for this purpose include promoters from glucocorticoid receptor genes (Aoyama and Chau, *Plant J* 11:605–12 (1997)). Tissue-specific promoters may only promote transcription within a certain time frame of developmental stage within that tissue. Other tissue specific promoters may be active throughout the life cycle of a particular tissue. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

A number of tissue-specific promoters can be used in the invention. Preferred promoter are those that direct expression of nucleic acids in seeds, for example, promoters from the DHN alleles of the invention. As used herein a seed-specific promoter is one which directs expression in seed tissues, such promoters may be, for example, ovule-specific, embryo-specific, endosperm-specific, integument-specific, seed coat-specific, or some combination thereof. Examples include a promoter from the ovule-specific BEL1 gene described in Reiser et al. *Cell* 83:735–742 (1995) (GenBank No. U39944). Other suitable seed specific promoters are derived from the following genes: MAC1 from maize (Sheridan et al. *Genetics* 142:1009–1020 (1996), Cat3 from maize (GenBank No. L05934, Abler et al. *Plant Mol. Biol.* 22:10131–1038 (1993), the gene encoding oleosin 18 kD from maize (GenBank No. J05212, Lee et al. *Plant Mol. Biol.* 26:1981–1987 (1994)), vivparous-1 from Arabidopsis (Genbank No. U93215), the gene encoding oleosin from Arabidopsis (Genbank No. Z17657), Atmyc1 from Arabidopsis (Urao et al. *Plant Mol. Biol.* 32:571–576 (1996), the 2s seed storage protein gene family from Arabidopsis (Conceicao et al. *Plant* 5:493–505 (1994)) the gene encoding oleosin 20 kD from *Brassica napus* (GenBank No. M63985), napA from *Brassica napus* (GenBank No. J02798, Josefsson et al. *JBL* 26:12196–1301 (1987), the napin gene family from *Brassica napus* (Sjodahl et al. *Planta* 197:264–271 (1995), the gene encoding the 2S storage protein from *Brassica napus* (Dasgupta et al. *Gene* 133:301–302 (1993)), the genes encoding oleosin A (Genbank No. U09118) and oleosin B (Genbank No. U09119) from soybean and the gene encoding low molecular weight sulphur rich protein from soybean (Choi et al. *Mol Gen, Genet.* 246:266–268 (1995)).

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *EMBO. J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as increased seed mass. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna, and Zea.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of MRNA or protein of the invention in transgenic plants, particularly in the seed. Means for detecting and quantitating mRNAs or proteins are well known in the art.

Plants with modulated seed germination can be easily be selected by monitoring seed germination using standard techniques.

EXAMPLES

The following examples are offered to illustrate, but not to limit the claimed invention.

MATERIALS AND METHODS

Development of Near-isogenic Lines and Emergence Test

Genetic lines were bred that would enable us to distinguish between nuclear and cytoplasmically inherited maternal effects associated with differences in electrolyte leakage while providing near-isogenic lines with and without the specific DHN. Reciprocal crosses were made between cowpea line 1393-2-11 and the genetically related line 1393-2-1. Replicates of the reciprocal $F_1$'s were backcrossed to 1393-2-1 and $BC_1F_1$ seeds were harvested and screened for the presence of the ~35-kDa DHN protein using an immunoblot assay of a chip taken from a cotyledon (Ismail et al., *Crop Sci.* 37:1270–1277 (1997)). Plants were propagated from seeds containing the DHN. The backcross and immunoblot assays were performed two more times. Plants were then allowed to self-pollinate. The $BC_3S_1$ families were screened for the presence of the DHN followed by three generations of selfing. Seeds of $BC_3S_4$ families were assayed for the presence of the DHN. Those originating from seeds in $BC_3S_1$ families that did not contain the DHN bred true for absence of the DHN. In addition, lines homozygous for the presence of the DHN were identified from those originating from $BC_3S_1$ seeds with the DHN. One pair of $BC_3S_4$ lines with individuals either having or not having the DHN in their seed was chosen from each of the original reciprocal crosses in the cytoplasms of 1393-2-11 and 1393-2-1.

Seeds from the two pairs together with the two parental lines were incubated over a saturated solution of lithium chloride for four weeks to reduce seed moisture content to 6% on a fresh weight bases (Ismail et al., *Crop Sci.* 37:1270–1277 (1997)). Samples of 10 seeds per line were tested for electrolyte leakage from individual seeds at 14° C. (G-2000 Seed Analyzer, Wavefront Inc., Ann Arbor, Mich.). Seeds were also tested for emergence at 14° C. in reach-in growth chambers in the dark as described before (Ismail et al., *Crop Sci.* 37:1270–1277 (1997)).

Construction and Screening of the cDNA Expression Library

Cowpea pods were harvested from line 1393-2-11 at the color break stage. At this stage there is a low but detectable level of the ~35 kDa DHN in developing seeds of this genotype (Ismail et al., *Plant Physiol.* 120, 237–244 (1999)). Seeds were ground to a fine powder in liquid nitrogen. Total RNA was prepared using the method of Verwoerd et al. (Verwoerd et al., *A. Nucleic Acids Res.* 17:2362 (1989)). Poly $(A)^+$ MRNA was isolated from total RNA using Promega polyATtract MRNA isolation system IV (Promega, Madison Wis.) and then converted to a double stranded cDNA using Stratagene ZAP Express cDNA synthesis kit (Stratagene Cloning Systems, La Jolla, Calif.).

About 100 ng of the cDNA was ligated to EcoR1-predigested ZAP express vector, then packaged in vitro using the Gigapack III gold packaging extract (Stratagene Cloning Systems, La Jolla, Calif.). The library contained a total of 2.1×106 pfU. Plaques were lifted using nitrocellulose membrane and screened using affinity purified anti-dehydrin antibodies (Close et al., *Plant Mol. Biol.* 23:279–286 (1993)).

Phagemid Excision and DNA Sequencing

Thirty-five positive clones were selected and further purified. Phagemids from four positive clones were excised in vivo from the Lambda ZAP vector using a helper phage (Stratagene Cloning Systems, La Jolla, Calif.). Phagemid DNAs were isolated by an alkaline lysis method (Sambrook et al., *Molecular Cloning: a Laboratory Manual*, 2nd edn (Cold Spring Harbor, N.Y.) (1989)) from 25 ml overnight cultures. DNA inserts from the four clones were sequenced on both strands using the dideoxy chain termination method. The nucleotide sequences and deduced amino acid sequences were analyzed using the DNASIS and PROSIS programs (Hitachi Software Engineering, San Bruno, Calif.).

Genomic DNA Amplification

A gene-specific oligonucleotide primer set was designed, composed of GGATCAGGGTTGCAAGATCGAC (5'-primer; SEQ ID NO:3) and CCCTTACGTTGGAGCCAACACC (3'-primer; SEQ ID NO:4) using PRIMER-MASTER program. Primers were synthesized by Genosys (The Woodlands, Tex.). Genomic DNA was isolated from etiolated young shoots using DNAzol® following the instructions provided by the manufacturer (Life Technologies, Gaithersburg, Md.). Genomic DNA was prepared from parental cowpea lines 1393-2-11 and 524B, whose seeds contain the ~35-kDa DHN, parental lines 1393-2-1 and IT84S-2049, whose seeds do not contain the ~35 kDa DHN, a set of 79 recombinant inbred lines and the two pairs of near-isogenic lines developed by backcrossing. The recombinant inbred lines came from a cross involving 524B and IT84S-2049 and were previously used to develop a cowpea linkage map (Menéndez et al., *Theor. Appl. Genet.* 95:1210–1217 (1997)). Genomic DNA amplifications were performed using a GeneAmp PCR System 9600 (Perkin Elmer, Foster City, Calif.) in 50 μl reaction containing 1.25 units of Taq DNA polymerase (Qiagen, Valencia, Calif. USA), 1×PCR buffer (10 mM Tris-HCl pH 8.3, 50 mM $KCl_2$, 1.5 mM $MgCl_2$), 0.4 μM primer, 200 μM each of dNTP, and 200 ng of genomic DNA from each of the cowpea lines. PCR reactions were started at 95° C. for 5 min, followed by 30 cycles of 95° C. for 30 sec, 62.4° C. for 30 sec and 72° C. for one min. The reaction was then terminated at 72° C. for 10 min. PCR products were analyzed using 1.5% agarose gels. The PCR-products from the four parental lines were purified using QIAquick PCR purification kit (Qiagen, Valencia, Calif. USA) and then sequenced on both strands in their entirety, using the dideoxy chain termination method.

RESULTS

Emergence of the Near-isogenic Lines at Low Temperature.

Figure 1:
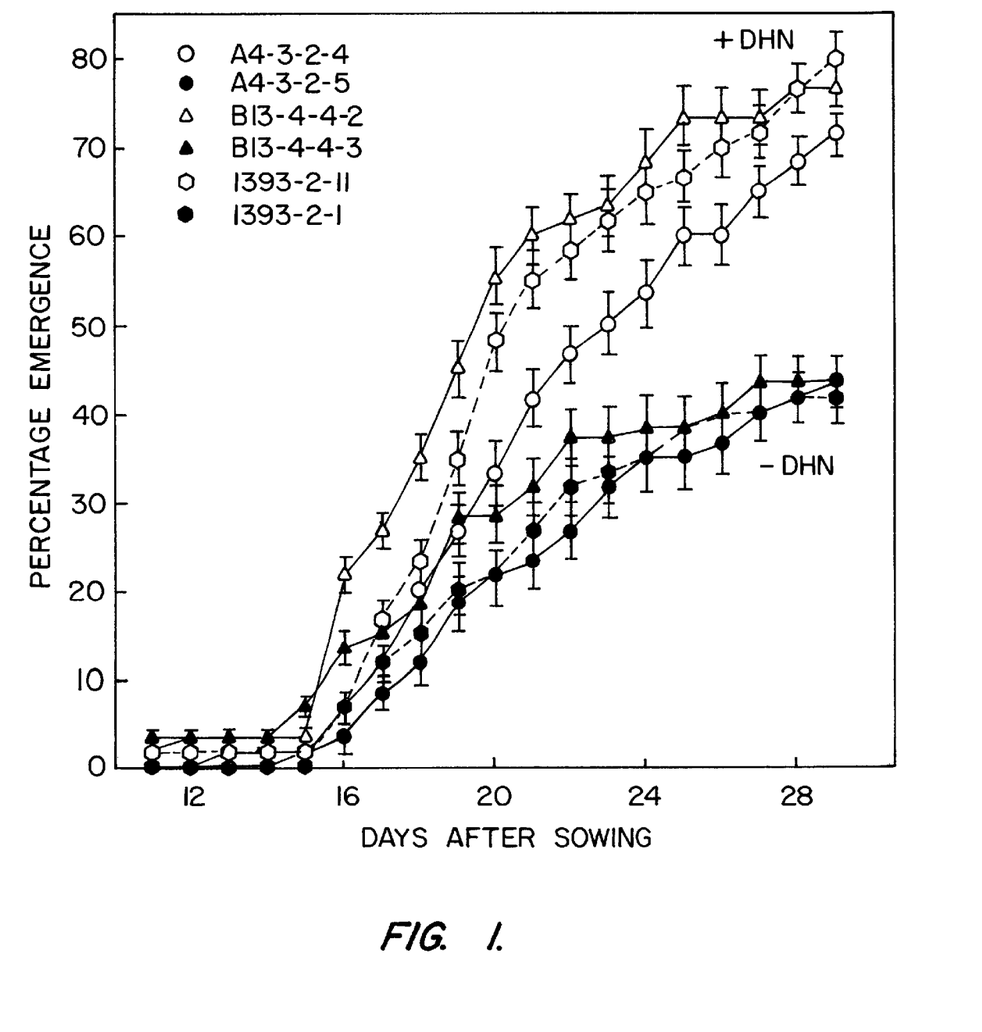
FIG. 1 shows percentage emergence of cowpea lines with (open symbols) or without (closed symbols) the ~35-kDa DHN at 14° C. using seeds with 6% moisture content. Parental lines are indicated by dotted lines and the vertical bars are the standard errors.

We evaluated the chilling tolerance of two pairs of near-isogenic lines together with their parents. The first pair consists of A4-3-2-4 (DHN present) and A4-3-2-5 (DHN absent) with the cytoplasm of 1393-2-11 in the 1393-2-1 genetic background, and the second pair consists of lines B13-4-4-2 (DHN present) and B13-4-4-3 (DHN absent) with the cytoplasm and genetic background of 1393-2-1. The genetic similarity between each pair of isolines should be greater than 99% since the original parental lines were $F_6$ siblings and they were then backcrossed three times to provide the isolines. Emergence of the seeds of the two pairs of near-isogenic lines and parents were determined at 14° C. Lines containing the DHN had significantly greater (33 percentage points) maximal emergence than lines not having the DHN (FIG. 1). These results provide strong support for the hypothesis that the ~35-kDa DHN protein confers an increment of chilling tolerance during emergence in cowpea. It should be noted that these cowpea seeds had 6% moisture content and would be more sensitive to chilling than seeds with higher moisture contents, such as 12%, which is typical of commercial seed (Ismail et al., *Crop Sci.* 37:1270–1277 (1997)). Although this chilling tolerance trait is more pronounced with drier seed, it is present at the higher moisture contents typical of commercial seed (Ismail et al., *Crop Sci.* 37:1270–1277 (1997)).

Cloning and Sequencing of the ~35-kDa DHN cDNA.

Previously, we had purified and partially characterized the cowpea ~35-kDa DHN (Ismail et al., *Plant Physiol.* 120, 237–244 (1999)) and shown that its presence/absence in seeds mapped as a single gene on a cowpea linkage map (Menéndez et al., *Theor. Appl. Genet.* 95:1210–1217 (1997)). Our objective here was to determine whether the presence/absence of this DHN in the mapping population is due to allelic variation in a Dhn structural gene or a trans-acting Dhn regulatory locus. For this purpose, it was necessary to identify a cDNA encoding this protein and develop a gene-specific probe. A cDNA expression library was constructed using poly (A) RNA from developing seeds. The cDNA expression library was screened using affinity-purified anti-dehydrin antibodies (Close et al., *Plant Mol. Biol.* 23:279–286 (1993)). Approximately 7% of all cDNA plaques were immuno-positive. A representative set of plaques was then purified and used for further analysis by DNA sequencing. The cDNA phagemids were excised from the lambda ZAP vector and four cDNAs were sequenced. The four cDNAs were found to be identical to each other in sequence except for the position of the poly (A) site and the 5' end, which is similar to observations made before with cereal Dhn cDNAs (Close et al., *Plant Mol. Biol.* 13:95–108 (1989)). The deduced amino acid sequence contained the polypeptide identified by partial amino acid sequencing of a CNBr fragment (Ismail et al., *Plant Physiol.* 120, 237–244 (1999)) of the ~35-kDa DHN protein (the last two T residues in Ismail et al., *Plant Physiol.* 120, 237–244 (1999) are now considered to be spurious). One sequence was submitted to GenBank (accession AF159804). A high similarity, but not 100% identity, was observed between this Dhn cDNA and a previously published Dhn cDNA sequence, CPRD22, from cowpea leaves subjected to dehydration (Iuchi et al., *Plant Cell Physiol.* 37:1073–1082 (1996)).

Figure 2:
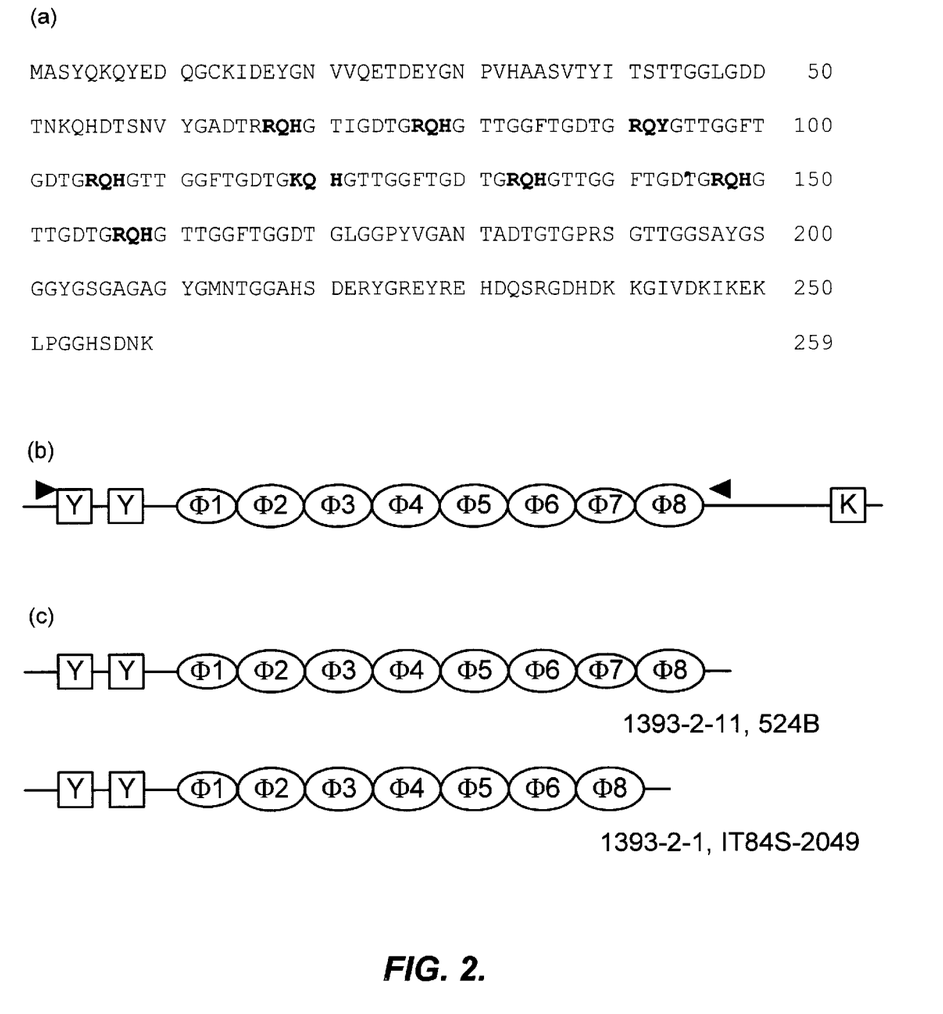

The deduced amino acid sequence of the 1393-2-11 Dhn cDNA is shown in FIG. 2a. The encoded protein consists of 259 amino acids (actual MW of 26.5 kDa compared with an apparent MW on SDS-PAGE of 35 kDa; an actual MW 24% smaller than the apparent MW on SDS-PAGE is typical of DHNs). Following the nomenclature scheme proposed by Close (Close, T. J., *Physiol. Plant.* 100:291–296 (1997)), this DHN is referred to as a $Y_2K$ DHN because it has two Y-segments near the N-terminus and one K-segment near the C-terminus. There are 8 Φ-segments between the distal Y-segment and the K-segment, two of which are smaller (10 amino acid residues) and six larger (14 amino acid residues) (FIG. 2b). The polypeptide is rich in Gly (25.9%), Thr (16.6%) and Asp (8.5%) and is acidic (pI=5.98). We refer to this protein as *Vigna unguiculata* DHN1 (1393-2-11, 259) following the allele nomenclature of Choi et al. (Choi et al., *Theor. Appl. Genet.* 98:1234–1247 (1999)).

Mapping of the Structural Gene.

Figure 3:
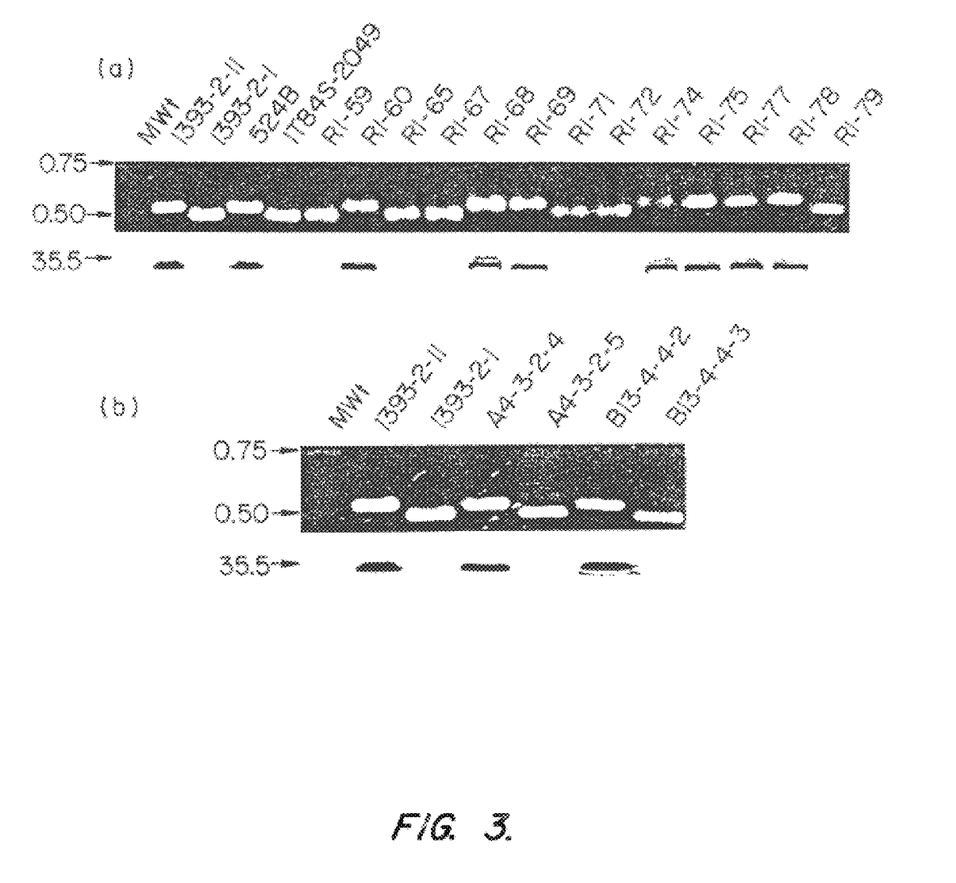
FIG. 3 shows PCR products (top) and western blots (bottom) from (a) parental cowpea lines and a subset of the recombinant inbred (RI) lines and (b) cowpea near-isogenic lines and parents. Total DNA was isolated from etiolated young shoots for PCR analysis. Total protein was extracted from dry, mature seeds for western blot analysis.

In order to map the structural gene encoding the $Y_2K$ DHN, gene-specific primers were designed from the nucleotide sequence and used to detect a polymorphism between cowpea lines, using PCR. Inbred lines 524B (DHN present) and IT84S-2049 (DHN absent) were the parents of a set of recombinant inbred lines (RILs) used for a cowpea linkage map (Menéndez et al., *Theor. Appl. Genet.* 95:1210–1217 (1997)). The Dhn1-specific primer set amplified a single major PCR product from each of the two lines, and yielded a higher MW band from the line with the $Y_2K$ DHN in the seed than from the one without it (FIG. 3a). Genomic DNA from a set of 79 RILs developed from IT84S-2049 and 524B were screened using these primers and a subset of the results is shown in FIG. 3a. A 100% co-segregation was observed between the DHN protein and the PCR products, indicating that both the locus controlling the presence/absence of the DHN protein and the structural Dhn gene map to the same position or are tightly linked.

The two parental lines 1393-2-11 and 1393-2-1 were used for developing the near-isogenic lines used in this study. The near-isogenic lines and parents (six total lines) were examined using the same PCR primers. Similar to the RILs, PCR products from DHN positive lines yield a higher MW band compared to those without the DHN (FIG. 3b).

To further define the allelic variation in the Dhn gene between DHN-positive and DHN-negative cowpea lines, PCR products from the four parental lines were purified and sequenced. Two types of allelic variation were identified at the protein level: deletion of one Φ-segment ($Φ_7$) from the DHN-negative lines (FIG. 2c) and two single-amino acid substitutions (T replaced by S, and K replaced by R, in the DHN-negative lines).

Electrolyte Leakage from Seeds of the Near-isogenic Lines.

Electrolyte leakages under chilling conditions from seeds of the first pair of near-isogenic lines A4-3-2-4 and A4-3-2-5 were 153 and 133 mS m$^{-1}$g$^{-1}$, and from the second pair B13-4-4-2 and B13-4-4-3 were 134 and 158 mS m$^{-1}$g$^{-1}$, respectively. The two parents 1393-2-11 and 1393-2-1 had electrolyte leakages of 104 and 143 mS m$^{-1}$g$^{-1}$, respectively, and the LSD$_{0.05}$ was 20 mS m$^{-1}$g$^{-1}$. These data indicate that electrolyte leakages from seeds of lines derived from both backcrosses were high and statistically similar to that of the recurrent parent, 1393-2-1, indicating nuclear inheritance and independence from the presence or absence of the DHN which is also under nuclear control. These results confirmed our previous model (Ismail et al., *Crop Sci.* 37:1270–1277 (1997)) in regards to independence of the DHN protein effect on chilling tolerance and differences in electrolyte leakage, and excluded cytoplasmic inheritance as the basis of the maternal effect on electrolyte leakage.

DISCUSSION

In previous studies we found that there is a genetic association between the presence of a ~35-kDa protein in mature seed and chilling tolerance during seedling emergence of cowpea line 1393-2-11 (Ismail et al., *Crop Sci.* 37:1270–1277 (1997)). Accumulation of this protein in developing seeds is coordinated with the start of the dehydration phase of embryo development, and the characteristics of the purified protein indicated that it is a DHN (Ismail et al., *J. Plant Physiol.* 120, 237–244 (1999)). Among other properties, this DHN has been found (Ismai et al., T. J. *Plant Physiol.* 120, 237–244 (1999)) to adhere to other polypeptides under specific salt conditions and also to adopt an α-helical structure in the presence of SDS.

Here we provide genetic evidence of the association between the structural gene, Dhn1, encoding this DHN protein and the chilling tolerance trait. Two types of allelic variations in the Dhn1 gene were identified at the protein level; deletion of one Φ-segment from the DHN-negative lines and two amino acid substitutions. These types of allelic variations are similar to differences observed between Dhn alleles in barley, where it was noted that the most common allelic variations involve deletions or duplications of entire Φ-segments or single amino acid substitutions (Choi et al., *Theor. Appl. Genet.* 98:1234–1247 (1999)). The genetic mechanism responsible for the presence/absence of DHN1 in mature seed is not yet known, but could involve differences in gene regulation. We can be confident that the DHN1 protein encoded by the "absence" allele is not produced in seed because the antibodies that detected the "presence" allele are specific to the K-segment (Close et al., *Plant Mol.*

Biol. 23:279–286 (1993)), and the K-segment is identical in both allelic forms of the DHN1 protein. In addition, others have shown that the "absence" allele of Dhn1 can indeed be expressed in other tissues; Dhn1 mRNA (CPRD22) is expressed in leaves of plants subjected to drought (Iuchi et al., *Plant Cell Physiol.* 37:1073–1082 (1996)). Consequently, the allelic difference that was used to study the inheritance of the Dhn1 gene (variable number of φ segments) seems unlikely to be the basis of the phenotypic effect. In addition, we cannot yet fully exclude the possibility that a gene mapping very near to the Dhn1 gene is the true phenotypic determinant, in which case it could be only coincidental that there is allelic variation in the Dhn1 gene, and strong expression of the DHN1 protein in close parallel with the seed properties.

The mechanism whereby the ~35-kDa DHN protein enhances chilling tolerance during emergence may not be related to the protection of plasma membrane since the effect was not associated with differences in electrolyte leakage. Previous studies provided evidence in favor of the presence of lipid-binding amphipathic α-helices in DHN proteins (Ismail et al., T. J. *Plant Physiol.* 120, 237–244 (1999)). The propensity of this DHN to adopt α-helical structure in the presence of sodium dodecyl sulfate together with its apparent polypeptide adhesion suggests that it may be exerting its effect through the stabilization of proteins in an endomembrane environment. This DHN, and others, may function biochemically in a manner similar to α-synuclein, which is a protein linked to both Parkinson's and Alzheimer's diseases, in the former as the major component of Lewy bodies and in the latter as a non-amyloid component of amyloid plaques (Davidson et al., *J. Biol. Chem.* 273:9443–9449 (1998)). α-synuclein is a small soluble protein of 140–143 amino acids, which is highly enriched in presynaptic nerve terminals, but not tightly associated with either the synaptic vesicle or the synaptic plasma membrane. Like the ~35-kDa DHN (Ismail et al.,. *Plant Physiol.* 120, 237–244 (1999)), α-synuclein appears in solution to have a largely random conformation, unless associated with negatively charged sulfonated- or phospho-lipids, in which case the protein contains α-helices (Davidson et al., *J. Biol. Chem.* 273:9443–9449 (1998)). Presumably then, the mode of action of the $Y_2K$ cowpea DHN involves a comparable type of phospholipid bilayer surface interaction (within the interior of the cell, but not the plasma membrane) that minimizes dehydration-associated lesions which can result in diminished emergence of seedlings at low temperature.

To our knowledge, co-segregation of the $Y_2K$ Dhn gene with chilling tolerance during emergence represents the first case where the functional significance of allelic variation in a stress-related gene has been strongly implicated by inheritance data in plants. Since there are several other classes of LEA, COR, etc. proteins in plants, and since several that have been studied have similar conformational and compositional properties to DHNs (Close, T. J., *Physiol. Plant.* 97:795–803 (1996); Thomashow, M., *Plant Physiol.* 118:1–8 (1998)), it seems likely that further studies of natural allelic variation in genes encoding these proteins will explain different facets of heritable variation in stress tolerance.

What is claimed is:

1. An isolated nucleic acid molecule comprising a polynucleotide sequence encoding a polypeptide that enhances chilling tolerance in plants, wherein the polynucleotide sequence comprises a sequence at least 90% identical to SEQ ID NO:1.

2. A recombinant expression vector comprising the polynucleotide sequence of claim 1.

3. The recombinant expression vector of claim 2, further comprising a promoter operably linked to the isolated nucleic acid molecule.

4. The recombinant expression vector of claim 3, wherein the promoter is a seed-specific promoter.

5. The recombinant expression vector of claim 3, wherein the promoter is an inducible promoter.

6. A host cell transformed with the recombinant expression vector of claim 2.

7. A transgenic plant comprising a recombinant expression cassette comprising a promoter operably linked to the isolated nucleic acid molecule claim 1.

8. The transgenic plant of claim 7, wherein the plant is cowpea.

* * * * *

SEQUENCE LISTING

<160> NUMBER OF SEQ ID NOS: 4

<210> SEQ ID NO 1
<211> LENGTH: 1149
<212> TYPE: DNA
<213> ORGANISM: Vigna unguiculata
<220> FEATURE:
<221> NAME/KEY: CDS
<222> LOCATION: (31)..(810)
<223> OTHER INFORMATION: DHN1 (1393-2-11, 259)

<400> SEQUENCE: 1

```
aaagttctta taatcacaac aacaacaacc atg gca agt tac cag aag cag tac      54
                                    Met Ala Ser Tyr Gln Lys Gln Tyr
                                     1               5 gag gat cag ggt tgc aag atc gac gag tat ggc aac gtt gta cag gaa      102
Glu Asp Gln Gly Cys Lys Ile Asp Glu Tyr Gly Asn Val Val Gln Glu
        10                  15                  20 act gat gaa tat ggc aac ccg gtt cat gca gca agt gtc acc tac ata      150
Thr Asp Glu Tyr Gly Asn Pro Val His Ala Ala Ser Val Thr Tyr Ile
 25                  30                  35                  40 acc tcc acc acc ggt ggt ctt ggg gat gac act aac aag caa cat gat      198
Thr Ser Thr Thr Gly Gly Leu Gly Asp Asp Thr Asn Lys Gln His Asp
                 45                  50                  55 acc agt aat gtc tac ggt gca gac acc cgt aga cag cac gga act ata      246
Thr Ser Asn Val Tyr Gly Ala Asp Thr Arg Arg Gln His Gly Thr Ile
             60                  65                  70 ggt gac acc ggt aga cag cac gga act acc ggt ggt ttt act ggt gac      294
Gly Asp Thr Gly Arg Gln His Gly Thr Thr Gly Gly Phe Thr Gly Asp
 75                  80                  85
```

```
acc ggt aga caa tat ggc act acc gga ggc ttt acc ggt gac acc ggg     342
Thr Gly Arg Gln Tyr Gly Thr Thr Gly Gly Phe Thr Gly Asp Thr Gly
         90                  95                 100 aga caa cat ggg act acc ggt ggt ttt acc ggt gac act ggg aaa caa     390
Arg Gln His Gly Thr Thr Gly Gly Phe Thr Gly Asp Thr Gly Lys Gln
105                 110                 115                 120 cat ggg act acc ggt ggt ttt acc ggt gac act ggg aga caa cat ggg     438
His Gly Thr Thr Gly Gly Phe Thr Gly Asp Thr Gly Arg Gln His Gly
                125                 130                 135 act act ggt ggt ttt acc ggt gac act ggg aga caa cat ggg act acc     486
Thr Thr Gly Gly Phe Thr Gly Asp Thr Gly Arg Gln His Gly Thr Thr
            140                 145                 150 ggt gac act ggg aga caa cat ggg act acc ggc ggc ttt act ggt ggt     534
Gly Asp Thr Gly Arg Gln His Gly Thr Thr Gly Gly Phe Thr Gly Gly
        155                 160                 165 gac act ggt ctg gga ggc cct tac gtt gga gcc aac acc gct gac aca     582
Asp Thr Gly Leu Gly Gly Pro Tyr Val Gly Ala Asn Thr Ala Asp Thr
    170                 175                 180 ggg act ggt cct aga agt gga acc aca ggt ggc agc gcc tat gga tcg     630
Gly Thr Gly Pro Arg Ser Gly Thr Thr Gly Gly Ser Ala Tyr Gly Ser
185                 190                 195                 200 ggt ggt tat gga agt gga gct gga gct ggg tat ggt atg aac acg ggg     678
Gly Gly Tyr Gly Ser Gly Ala Gly Ala Gly Tyr Gly Met Asn Thr Gly
                205                 210                 215 gga gca cac agt gat gaa agg tat gga agg gag tat cgt gag cat gat     726
Gly Ala His Ser Asp Glu Arg Tyr Gly Arg Glu Tyr Arg Glu His Asp
            220                 225                 230 cag tct cgt gga gat cat gac aag aaa ggg ata gtg gac aag att aag     774
Gln Ser Arg Gly Asp His Asp Lys Lys Gly Ile Val Asp Lys Ile Lys
        235                 240                 245 gag aag ctt ccc gga gga cac agt gac aac aag tag agacatcatg          820
Glu Lys Leu Pro Gly Gly His Ser Asp Asn Lys
    250                 255                 260 ggtgtgcatg catgcgtata tatacgtagt ataattaaag atgttatatt gttgtgtttt   880
tgaataagtt tgctgcatat atacgtactc gtacagtact gtcttgtcgt gtaaatgtgg   940
tggatcttgt atatggttat agtatatgca agaggaataa aaggtgcatg catgcaagag  1000
aaagaaggca tagatgttct gccaatggaa agtaaaaacc taccctgatg tagagcaggg  1060
tgcttcagtt gtgtgttttt gaattttcca atgaagcaag ttttttcttta aaaaaaaaa  1120 aaaaaaaaa aaaaaaaaaa aaaaaaaa                                     1149
```

<210> SEQ ID NO 2
<211> LENGTH: 259
<212> TYPE: PRT
<213> ORGANISM: Vigna unguiculata

<400> SEQUENCE: 2

```
Met Ala Ser Tyr Gln Lys Gln Tyr Glu Asp Gln Gly Cys Lys Ile Asp
1               5                  10                  15

Glu Tyr Gly Asn Val Val Gln Glu Thr Asp Glu Tyr Gly Asn Pro Val
            20                  25                  30

His Ala Ala Ser Val Thr Tyr Ile Thr Ser Thr Thr Gly Gly Leu Gly
        35                  40                  45

Asp Asp Thr Asn Lys Gln His Asp Thr Ser Asn Val Tyr Gly Ala Asp
    50                  55                  60

Thr Arg Arg Gln His Gly Thr Ile Gly Asp Thr Gly Arg Gln His Gly
65                  70                  75                  80
```

```
Thr Thr Gly Gly Phe Thr Gly Asp Thr Gly Arg Gln Tyr Gly Thr Thr
                85                  90                  95

Gly Gly Phe Thr Gly Asp Thr Gly Arg Gln His Gly Thr Thr Gly Gly
            100                 105                 110

Phe Thr Gly Asp Thr Gly Lys Gln His Gly Thr Thr Gly Gly Phe Thr
        115                 120                 125

Gly Asp Thr Gly Arg Gln His Gly Thr Thr Gly Gly Phe Thr Gly Asp
    130                 135                 140

Thr Gly Arg Gln His Gly Thr Thr Gly Asp Thr Gly Arg Gln His Gly
145                 150                 155                 160

Thr Thr Gly Gly Phe Thr Gly Gly Asp Thr Gly Leu Gly Gly Pro Tyr
                165                 170                 175

Val Gly Ala Asn Thr Ala Asp Thr Gly Thr Gly Pro Arg Ser Gly Thr
            180                 185                 190

Thr Gly Gly Ser Ala Tyr Gly Ser Gly Gly Tyr Gly Ser Gly Ala Gly
            195                 200                 205

Ala Gly Tyr Gly Met Asn Thr Gly Gly Ala His Ser Asp Glu Arg Tyr
        210                 215                 220

Gly Arg Glu Tyr Arg Glu His Asp Gln Ser Arg Gly Asp His Asp Lys
225                 230                 235                 240

Lys Gly Ile Val Asp Lys Ile Lys Glu Lys Leu Pro Gly Gly His Ser
                245                 250                 255

Asp Asn Lys

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:
      gene-specific oligonucleotide 5'-primer

<400> SEQUENCE: 3
ggatcagggt tgcaagatcg ac                                          22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:
      gene-specific oligonucleotide 3'-primer

<400> SEQUENCE: 4
cccttacgtt ggagccaaca cc                                          22
```